United States Patent [19]

Grier et al.

[11] 4,149,983

[45] Apr. 17, 1979

[54] ANTIMICROBIAL ADDITIVE FOR METAL WORKING FLUIDS

[75] Inventors: Nathaniel Grier, Englewood; Bruce E. Witzel, Westfield, both of N.J.

[73] Assignee: Merck & Co., Inc., Rahway, N.J.

[21] Appl. No.: 892,724

[22] Filed: Apr. 3, 1978

[51] Int. Cl.$^2$ ............................................. C10M 1/06
[52] U.S. Cl. ................................. 252/49.5; 252/49.3; 252/51.5 R; 252/77; 424/249
[58] Field of Search ............... 252/49.3, 49.5, 51.5 R, 252/77; 424/249

[56] References Cited

U.S. PATENT DOCUMENTS

| | | | |
|---|---|---|---|
| 2,729,680 | 1/1956 | Anderson | 260/566 R |
| 2,953,564 | 9/1960 | Sherman | 424/249 X |
| 3,159,624 | 12/1964 | Kodama et al. | 424/249 X |
| 3,475,421 | 10/1969 | Chretien et al. | 424/249 X |
| 3,704,335 | 11/1972 | Kodama et al. | 424/249 |
| 3,759,828 | 9/1973 | Harrison | 252/49.5 X |
| 3,791,974 | 2/1974 | Borchert | 252/49.5 |
| 3,840,661 | 10/1974 | Waldstein | 252/51.5 R X |
| 3,915,970 | 10/1975 | Limaye et al. | 252/51.5 R X |
| 3,962,240 | 6/1976 | Bennett | 424/249 X |
| 4,033,886 | 7/1977 | Felton, Jr. | 252/49.5 X |

*Primary Examiner*—Delbert E. Gantz
*Assistant Examiner*—Andrew Metz
*Attorney, Agent, or Firm*—Edmunde D. Riedl; Mario A. Monaco

[57] ABSTRACT

Compositions of 1,3,5-tris-(furfuryl)hexahydro-s-triazine are useful as antimicrobial agents particularly when added to metal-working compositions subject to fungal and bacterial attack.

8 Claims, No Drawings

ANTIMICROBIAL ADDITIVE FOR METAL WORKING FLUIDS

This invention relates to new and useful compositions of 1,3,5-tris-(furfuryl)hexahydro-s-triazine. This invention, most particularly, relates to metal-working compositions protected against fungal and bacterial attack by including therein an anti-fungal and antibacterial amount of 1,3,5-tris-(furfuryl)hexahydro-s-triazine.

Metal-working fluids are employed both as lubricants and heat transfer agents in operations such as cutting, drilling, rolling, broaching, drawing, extruding, and grinding. There are three basic types of these fluids: straight, soluble and synthetic.

Straight fluids comprise petroleum oils and are used as single phase systems with only slight water content. The microbial degradation problems generally occur upon storage which allows an accumulation of water as from atmospheric condensation or rain.

Soluble fluids are usually naphthenic or paraffinic hydrocarbons formulated with surfactants and dispersants which produce oil-in-water emulsions on admixture with water. A variation is obtained to provide hydraulic fluids which are in reverse phase, that is, an emulsion containing water dispersed in the oil phase.

Synthetic fluids, the third type, generally comprise carboxylic and organic phosphate esters, chemically modified vegetable oils and the like replacing petroleum-based oils to provide in-use emulsions of which the external phase is water.

Additives are commonly a part of metal-working fluid formulations and include agents such as antifreeze, liquid coupling, antioxidants, corrosion inhibitors, metal deactivators, viscosity modifiers, antifoams, extreme-pressure modifiers, oiliness, anti-wear, pour-point depressants and more. Emulsions of oil and water also require as additives, wetting-agents, surfactants, chelators for hard water metal ions and stabilizers such as thickening agents.

Most of the constituents of metal-working fluids outlined when admixed with water serve as nutrients to support microbial growth.

Unless controlled, these organisms affect the performance of a fluid as, for example, by lowering the pH or breaking the emulsion. A low pH fluid is corrosive to metal and the resultant metal ions form precipitates with surfactants which tend to break down the emulsion. Whether or not the performance of the metal-working fluid is spoiled by bacterial or fungal action, it often becomes so foul smelling that it must be discarded. Such disposal, possibly involving thousands of gallons of a malodorous oily emulsion presents a considerable ecological problem and economic loss. Furthermore, there is an increasing trend toward the use of solubilized oils which are more susceptible to attack by microorganisms as compared to the straight mineral oils. Regulations on effluent discharges increase the need for metal-working fluids protected with efficient biocides, because untreated fluids go rancid more rapidly, requiring more frequent disposal and thus contributing to pollution.

A great variety of microorganisms are found in metal-working fluids, but the anaerobic sulfate reducers and fungi are particularly troublesome to control. Others include the aerobic gram-negative bacteria, e.g., coliforms, and particularly Pseudomonas. Actual spoilage of the fluids appears to be associated with Pseudomonas and sulfate reducing bacteria such as Desulfovibrio desulfuricans.

Heretofore, biocides used to protect metal-working fluids have included tris(hydroxymethyl)nitro-methane; organic iodine; hexamethylenetetramine derivatives; o-phenylphenol; sodium o-phenylphenate; sodium 2,4,5-trichlorophenate; 2,3,4,6-tetrachlorophenol; dimethoxane; 1,2-benzisothiazolin-3-one; hexahydro-1,3,5-tris-(2-hydroxyethyl)-s-triazine; and zinc pyridinethione. However, most have proven unsatisfactory because of narrow spectrum, potential toxicities, high cost or other important considerations. In practice, biocides are often added at least twice, first by the formulators of the fluids themselves for preservation and then by the user to additionally extend service life.

Under typical operating conditions, there are problems of contamination from organic matter, dirt, metal cuttings, and other debris. An ideal product would function properly despite this and present no environmental disposal problems. Therefore, the object of this invention is to provide a biocide for metal-working fluids which presents a minimum of environmental problems and can be used with a variety of metal working fluids to control the growth of undesirable organisms.

The biocidal metal working compositions of this invention comprise 0.1% to 5% by weight 1,3,5-tris-(furfuryl)hexahydro-s-triazine; from 40% to 99.9% by weight of a carrier fluid; and from 0% to 30% by weight of a surfactant. The carrier can comprise an organic solvent such as a $C_1$ to $C_8$ alkanol; a $C_8$ to $C_{22}$ alkane or alkene; a petroleum oil fraction having a boiling point of from 80° C. to 190° C; or an oil derived from a $C_{12}$ to $C_{18}$ fatty acid, a glycol such as glycerine, or ethylene glycol, or less desirably a ketone, e.g., methyl ethyl ketone or other ketone having a total carbon of $C_3$ to $C_8$ either alone or emulsified with water. Generally, at least 0.5% by weight of a surfactant is employed, especially in metal working fluids that comprise water, since the surfactant is indispensible as an emulsifying agent.

When employed as a premix, the compositions of this invention suitably comprise from 1% to 95% by weight 1,3,5-tris-(furfuryl)hexahydro-s-triazine and from 4% to 99% by weight of a carrier fluid and from 0% to 30% by weight of a surfactant. In preferred compositions, the carrier fluid comprises 50% to 99.5% by weight of the composition and is a hydrocarbon or petroleum fluid. It is suitable for this premix to be utilized in the form of an emulsion. Therefore, the premix composition can most suitably comprise 25% to 50% by weight water.

In other suitable compositions, the carrier fluid can comprise 50% or more by weight water. Where the carrier fluid is entirely water, it is essential that at least 0.5% by weight of a surfactant be employed.

This aqueous emulsion is especially suitable for use in aqueous based metal working fluids. Where desired, a premix comprising only hydrocarbon or petroleum based carrier fluid can be employed and this is most suitable where the metal working fluid is a composition excluding water. The preferred carriers are those which are substantially similar to the chemical composition of the hydrocarbon or petroleum based solvent employed in the cutting fluid.

The surfactant serves as an emulsifying agent and may be any conventional water-dispersible emulsifying agent or mixtures thereof preferably having a hydrophobic lipophilic balance (HLB) of at least 7. The preferred surfactants include ethoxylated nonyl phenols, ethoxylated nonylphenol formaldehyde resin, dioctyl esters of sodium sulfosuccinate, and octyl phenolpolyethoxy ethanol can be used.

Other surfactants that may be employed include the soaps such as sodium and potassium myristate, laurate, palmitate, oleate, stearate, resinate and hydroabietate, the alkali metal alkyl or alkylene sulfates, such as sodium lauryl sulfate, potassium stearyl sulfate, the alkali metal alkyl or alkylene sulfonates, such as sodium lauryl sulfonate, potassium stearyl sulfonate, and sodium cetyl sulfonate, sulfonated mineral oil, as well as the ammonium salts thereof; and salts of higher amines like lauryl amine hydrochloride and stearyl amine hydrobromide.

Any anionic, cationic, or nonionic compound can be used as the surfactant. Examples of desirable anionic surfactants are alkali metal, ammonium and amine soaps; the fatty acid part of such soaps contain preferably at least 16 carbon atoms because soaps based on lauric and myristic acids have a great tendency to develop abundant foam.

Other examples of desirable anionic surfactants are alkali metal salts of alkyl-aryl sulfonic acids, sodium dialkyl sulfosuccinate, sulfated or sulfonated oils, e.g., sulfated castor oil; sulfonated tallow and alkali salts of short chain petroleum sulfonic acids.

Examples of suitable cationic surfactants are salts of long chain primary, secondary, or tertiary amines, such as oleylamine acetate, cetylamine acetate, didodecylamine lactate, the acetate of aminoethyl stearamide, dilauroyl triethylene tetraamine diacetate, 1-aminoethyl-2-heptadecenyl imidazoline acetate; and quaternary salts, such as cetylpyridinium bromide, hexadecyl ethyl morpholinium chloride, and diethyl didodecyl ammonium chloride.

Examples of suitable nonionic surfactants are condensation products of higher fatty alcohols with ethylene oxide, such as the reaction product of oleyl alcohol with 10 ethylene oxide units; condensation products of alkyl phenols with ethylene oxide, such as the reaction products of isooctylphenol with 12 ethylene oxide units; condensation products of higher fatty acid amides with five, or more, ethylene oxide units; polyethylene glycol esters of long chain fatty acids, such as tetraethylene glycol monopalmitate, hexaethyleneglycol monolaurate, nonethyleneglycol monostearate, nonethyleneglycol dioleate, tridecaethyleneglycol monoarachidate, tricosaethyleneglycol monobehenate, tricosaethyleneglycol dibehenate, polyhydric alcohol partial higher fatty acid esters such as sorbitan tristearate, ethylene oxide condensation products of polyhydric alcohol partial higher fatty esters, and their inner anhydrides (mannitol anhydride, called Mannitan, and sorbitol-anhydride, called Sorbitan), such as glycerol monopalmitate reacted with 10 molecules of ethylene oxide, pentaerythritol monooleate reacted with 12 molecules of ethylene oxide, sorbitan monostearate, reacted with 10 to 15 molecules of ethylene oxide; long chain polyglycols in which one hydroxyl group is esterified with a higher fatty acid and the other hydroxy group is etherified with a low molecular alcohol, such as methoxypolyethylene glycol 550 monostearate (550 meaning the average molecular weight of the polyglycol ether). A combination of two or more of these surfactants may be used; e.g., a cationic may be blended with a nonionic or an anionic with a nonionic.

Following is a list of suitable surfactants that could be used in the practice of this invention. Any water-dispersible surfactant could be used, but naturally some are more efficient than others. Useful surfactants include, but are not limited to, Sorbitan sesquioleate, polyoxyethylene alkyl phenol, polyoxyethylene (10 mole) cetyl ether, polyoxyethylene alkylaryl ether, polyoxyethylene monolaurate, polyoxyethylene vegetable oil, polyoxyethylene sorbitan monolaurate, polyoxyethylene (40 mole) sorbitol hexaoleate, polyoxyethylene esters of mixed fatty and resin acids, polyoxyethylene sorbitol lanolin derivative, polyoxyethylene (12 mole) tridecyl ether, polyoxyethylene sorbitan esters of mixed fatty and resin acids, polyoxyethylene sorbitan monostearate, polyoxyethylene sorbitan monooleate, polyoxyethylene monostearate, polyoxyethylene (20 mole) stearyl ether, polyoxyethylene (20 mole) oleyl ether, polyoxyethylene (15 mole) tridecyl ether, polyoxyethylene fatty alcohol, polyoxyethylene alkyl amine, polyoxyethylene glycol monopamitate, polyoxyethylene sorbitan monopalmitate, polyoxyethylene (20 mole) cetyl ether, polyoxyethylene oxypropylene stearate, polyoxyethylene lauryl ether, polyoxyethylene lanolin derivative, sodium oleate, quaternary ammonium derivative, potassium oleate, N-ethyl morpholinium ethosulfate, and pure sodium lauryl sulfate. Prior art processes, as illustrated by U.S. Pat. No. 3,284,393, utilize significantly lower amounts of emulsifying agents and produce products that are less storage stable and have less freeze/thaw stability.

An oil phase if included can be any inert hydrophobic liquid. A preferred group of organic liquids are the hydrocarbon liquids which include both aromatic and aliphatic compounds. Thus, such organic hydrocarbon liquids as xylene, toluene, mineral oils, mineral spirits, kerosenes and naphthas can be employed. Preferred oils include Mentor 28, a high boiling paraffinic mineral oil marketed by Exxon and Soltrol 200 and Sortrol 220, high boiling paraffinic mineral oils marketed by Phillips Petroleum Company.

Where an emulsion is employed, the amount of oil used in relation to the water to prepare the emulsion may be varied over wide ranges. As a general rule, the amount of water-to-oil may vary between 40:1 to 1:10 with the preferred amount of water-to-oil being in the ratio of 1:1 to 20:1. These ratios are illustrative of emulsions that can be prepared, although it should be understood that the invention is not limited thereby.

The compositions of metal-working fluids can vary broadly depending upon applications. Generally, preferred utility emulsifiable oils usually contain 80% to 90% by weight of a petroleum hydrocarbon oil, 5% to 18% of an emulsifying agent soluble in the oil which may be oleic acid, a sulfated mineral oil, a polyethoxylated substituted phenol and others, together with a small percentage, usually less than 2% of water to prevent gelling. When freezing point depressants are formulated into the oil base, and such agents include methyl alcohol, ethylene glycol, propylene glycol, dipropylene glycol or hexylene glycol, a sufficient quantity is used so that upon emulsification of the oil in from 10–50 parts of water per 1 part of oil there is present from 1 to 100 parts of freezing point depressant per 100 parts of water comprising the aqueous phase of the emulsion.

Extreme pressure additives commonly employed include graphite, molybdenum sulfide, sulfuretted oils, fatty amine salts of long chain phosphate acid esters, talc and others. Antioxidants are based primarily upon aromatic compounds containing an air-sensitive group such as hydroxy, amino or alkoxy along with oil-solubilizing alkyl ring substituents. 2,6-Ditert. butyl-phenol, N-butyl para-aminophenol, p-nonylphenol and 1,5-dihydroxynaphthalene are a few examples.

Corrosion inhibitors presently in popular use are presenting problems of potential toxicity. Apparently, morpholine and other secondary amines interact with inorganic nitrites also added as corrosion inhibitors to produce carcinogenic nitroso amines. Other corrosion inhibitors such as inorganic salts of 2-mercaptobenzothiazole, of alkenylsuccinic acids and of stearic acid, butyl esters of lipid-soluble carboxylic acids and various polysiloxanes will probably be preferably added.

Some representative compositions are:

| Cutting Fluid | Parts by Wt. |
|---|---|
| Triethanolamine | 20 |
| Caprylic Acid | 3 |
| Poly(oxyethylene)glycol | 7 |
| Sodium 2-Mercaptobenzothiazole | 3 |
| 1,3,5-Tris-(furfuryl)hexahydro-s-triazine | 0.5 |
| Water | 66.5 |

For use the fluid is diluted with water.

| | Parts by Wt. |
|---|---|
| Mineral Oil (d$_{20}$, 0.915) | 80 |
| Petroleum Sulfonate (mol. wt. 400) as 70% aq. solution | 14 |
| Ethoxylated (5 moles ethylene oxide) oleyl alcohol | 3.5 |
| 1,3,5-Tris-(furfuryl)hexahydro-s-triazine | 2 |
| 2,6-Ditertiarybutyl-p-cresol | 0.5 |

For use one part of the fluid is diluted with 20–40 parts of water.

| Grinding fluid | Parts by Wt. |
|---|---|
| Poly(ethoxylated) Castor Oil | 50 |
| Dipropylene Glycol | 50 |
| Water | 150 |
| 1,3,5-Tris-(furfuryl)hexahydro-s-triazine | 0.15–0.6 |

| | Parts by Wt. |
|---|---|
| Poly(ethoxylated) Castor Oil | 25 |
| Hexylene Glycol | 20 |
| Dipropylene Glycol | 45 |
| Petroleum Sulfonate | 5 |
| Poly(oxyethylene)octadecylamine | 2 |
| 1,3,5-Tris-(furfuryl)hexahydro-s-triazine | 0.3–1 |
| Dibenzyl Disulfide | 2 |
| Water | 600 |

| Mold Release Formulation | Parts by Wt. |
|---|---|
| Dow-Corning Co. Silicone Oil 200 (1000 centistoke) | 200 |
| Poly(Acrylic Acid) | 2 |
| Dodecylamine | 1 |
| Sodium Hydroxide (10% Solution) | 6 |
| 1,3,5-Tris-(furfuryl)hexahydro-s-triazine | 0.1–0.4 |
| Water | 200 |

HYDRAULIC FLUID - LUBRICANT

Oil-in-water emulsions are prepared from 80 parts water, 20–99 parts mineral oil and 0.2–10 parts ester obtained by a $C_{50+}$ alkylsubstituted succinic acid esterification with, for example, sorbitan monooleate or other polyols.

| | Parts by Wt. |
|---|---|
| Lubricating Oil SAE 30 | 286 |
| Soybean Lecithin | 1.8 |
| Zinc Diisooctylphosphorodithioate | 3 |
| Primary tert. $C_{11}$–$C_{14}$ alkylamine | 0.6 |
| Sorbitan Oleate, Polyisobutenyl-succinate | 9 |
| Silicone Antifoam | .0075 |
| 1,3,5-Tris-(furfuryl)hexahydro-s-triazine | 0.3–30 |

For use, these compositions can be diluted in water to provide a use concentration ranging from 1:1 to 1:100.

In use, the premix is added to a metal working oil fluid or to an existing emulsion, or less suitably to water. The emulsions obtained therefrom upon admixing the composition of this invention with water and/or an oil as hereinbefore defined so that a concentration of from 50 to 5000 parts per million of antimicrobial is obtained at final use dilutions. Generally, cutting oil concentrates are diluted with 10 to 50 parts by weight of water for end use application as for machining operations. At the lower dilution ratio, in round numbers, 10,000 ppm of the compounds of this invention would be contained in the oil concentrate so that upon addition of one part of oil to 9 parts of water a final concentration of 1,000 ppm would result. The antimicrobial can, if desired, also be added after dilution.

For mold release agents or hydraulic fluids, it is preferable to incorporate the antimicrobial during product formulation. These preparations usually contain sufficient water to promote microbial growths prior to usage and require protection against biodegradation in the package or on storage. The ingredients employed may carry microbial inocula or simply air-borne organisms may initiate growths.

Other aqueous systems which are vulnerable to microbial degradation and which may be protected against biodeterioration with the compositions of this invention include aqueous adhesives, pigment dispersions, paints, cooling tower systems, drilling muds, enhanced oil recovery brines and pusher fluids, papermill waters and as antimicrobials for pathogenic microorganisms on seeds and plants.

What is claimed is:

1. A composition for inhibiting the growth of microorganisms in metal working fluid comprising 0.5% to 55% by weight of 1,3,5-tris-(furfuryl)hexahydro-s-triazine; 40% to 99.5% by weight of a carrier fluid; and from 0.5% to 30% by weight of a surfactant.

2. A composition according to claim 1 where at least 50% by weight of the carrier fluid is water.

3. A composition suitable for used as a premix for addition to cutting oil fluids comprising from 1% to 95% by weight 1,3,5-tris-(furfuryl)hexahydro-s-triazine; 4% to 99% by weight of a carrier fluid; and from 0% to 30% by weight of a surfactant, provided that where the carrier fluid is water, at least 0.5% by weight of a surfactant is employed.

4. A composition according to claim 3 where the carrier fluid is a petroleum oil fraction having a boiling point from 80° C. to 190° C.

5. A composition according to claim 3 where the carrier fluid is 25% to 50% by weight water.

6. A composition according to claim 3 where the carrier fluid is at least 50% by weight water.

7. A method of inhibiting the growth of undesirable microorganisms in metal working fluids by admixing with said metal working fluids a microbial growth inhibiting amount of 1,3,5-tris-(furfuryl)hexahydro-s-triazine.

8. A method according to claim 7 where the 1,3,5-tris-(furfuryl)hexahydro-s-triazine is employed at a concentration of from 0.1% to 5% by weight.

* * * * *